US 6,742,544 B2

(12) United States Patent
Bergh et al.

(10) Patent No.: US 6,742,544 B2
(45) Date of Patent: Jun. 1, 2004

(54) INJECTION VALVE ARRAY

(75) Inventors: H. Sam Bergh, San Francisco, CA (US); Daniel M. Pinkas, Alameda, CA (US); Frank Doffing, Kastellaun (DE); Michael Klaus, Berlin (DE); Friedhelm Schoenfeld, Mainz (DE)

(73) Assignee: Symyx Technologies, Inc., Santa Clara, CA (US)

( * ) Notice: Subject to any disclaimer, the term of this patent is extended or adjusted under 35 U.S.C. 154(b) by 183 days.

(21) Appl. No.: 10/092,035

(22) Filed: Mar. 6, 2002

(65) Prior Publication Data

US 2002/0124897 A1 Sep. 12, 2002

Related U.S. Application Data

(60) Provisional application No. 60/274,022, filed on Mar. 7, 2001.

(51) Int. Cl.[7] ............................................. F16K 11/22
(52) U.S. Cl. ................................................... 137/885
(58) Field of Search .................. 73/863.71, 864.83, 73/23.41, 23.42

(56) References Cited

U.S. PATENT DOCUMENTS

| 3,057,376 | A | 10/1962 | Agutter et al. |
| 4,304,257 | A | 12/1981 | Webster |
| 4,869,282 | A | 9/1989 | Sittler et al. |
| 5,487,313 | A | 1/1996 | Johnson |
| 5,549,134 | A | 8/1996 | Browne et al. |
| 5,601,115 | A | 2/1997 | Broerman |
| 5,899,437 | A | 5/1999 | Quarre |
| 5,950,674 | A | 9/1999 | Wylie et al. |
| 6,007,046 | A | 12/1999 | Rothermel |
| 6,056,269 | A | 5/2000 | Johnson et al. |
| 6,126,140 | A | 10/2000 | Johnson et al. |
| 6,149,882 | A | 11/2000 | Guan et al. |
| 6,158,712 | A | 12/2000 | Craig |
| 6,251,343 | B1 * | 6/2001 | Dubrow et al. ............. 422/102 |

FOREIGN PATENT DOCUMENTS

| EP | 1 178 309 A1 | 2/2002 |
| WO | WO 00/23734 | 4/2000 |

OTHER PUBLICATIONS

International Search Report from the European Patent Office mailed Oct. 21, 2002.

* cited by examiner

*Primary Examiner*—John Fox
(74) *Attorney, Agent, or Firm*—Senniger, Powers, Leavitt & Roedel

(57) ABSTRACT

A novel gas injection valve for injecting discrete charges of gas into a mobile phase or carrier stream is provided. Injection valves of the invention comprise a plurality of microvalves capable of receiving gas at different pressures and emitting discrete charges of gas at approximately the same pressure. The invention further provides for parallel injection valve arrays capable of injecting multiple samples substantially simultaneously and a method of injecting discrete gas samples at a controlled pressure to a high-resolution gas chromatograph.

4 Claims, 16 Drawing Sheets

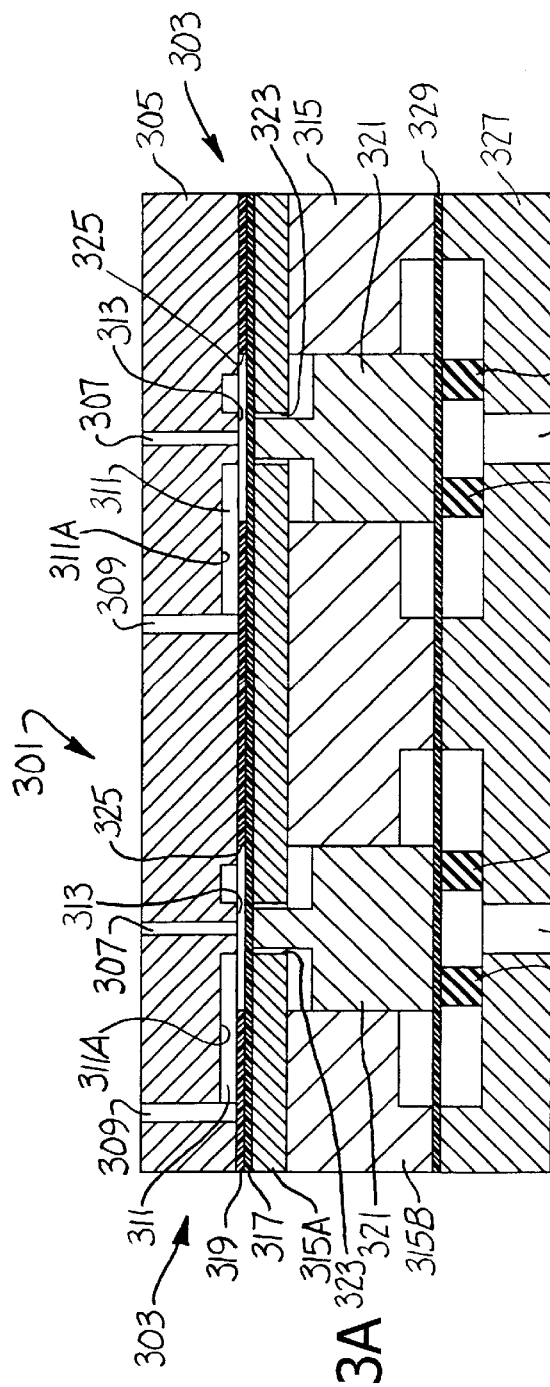
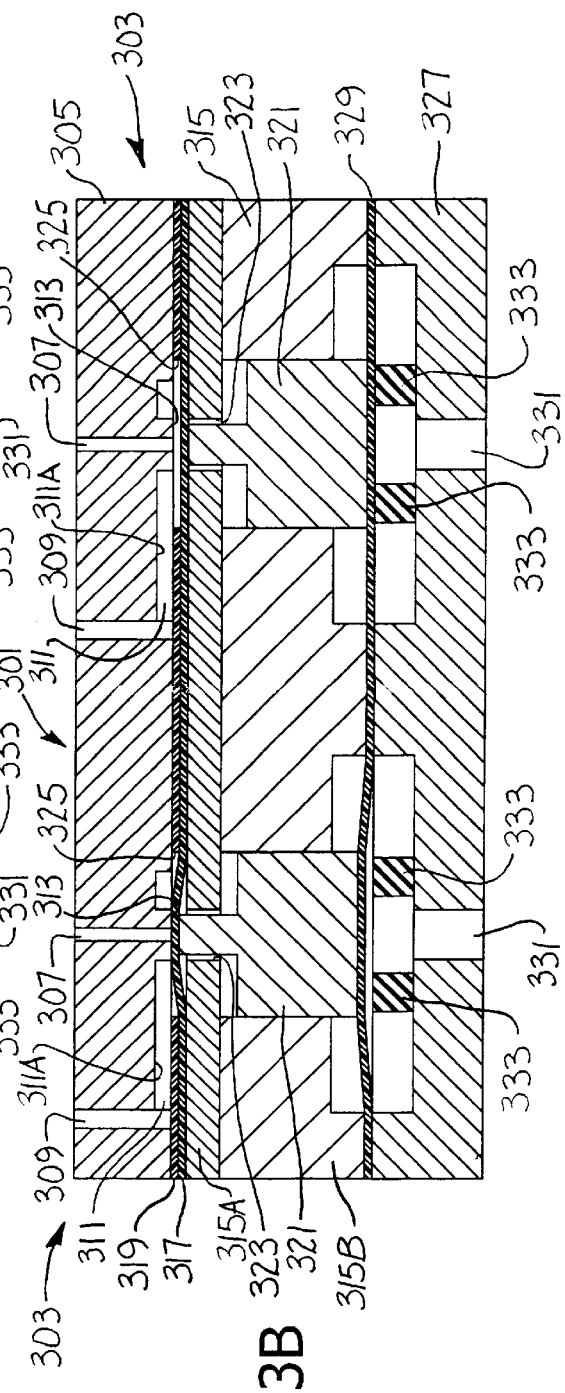
FIG. 3A
FIG. 3B

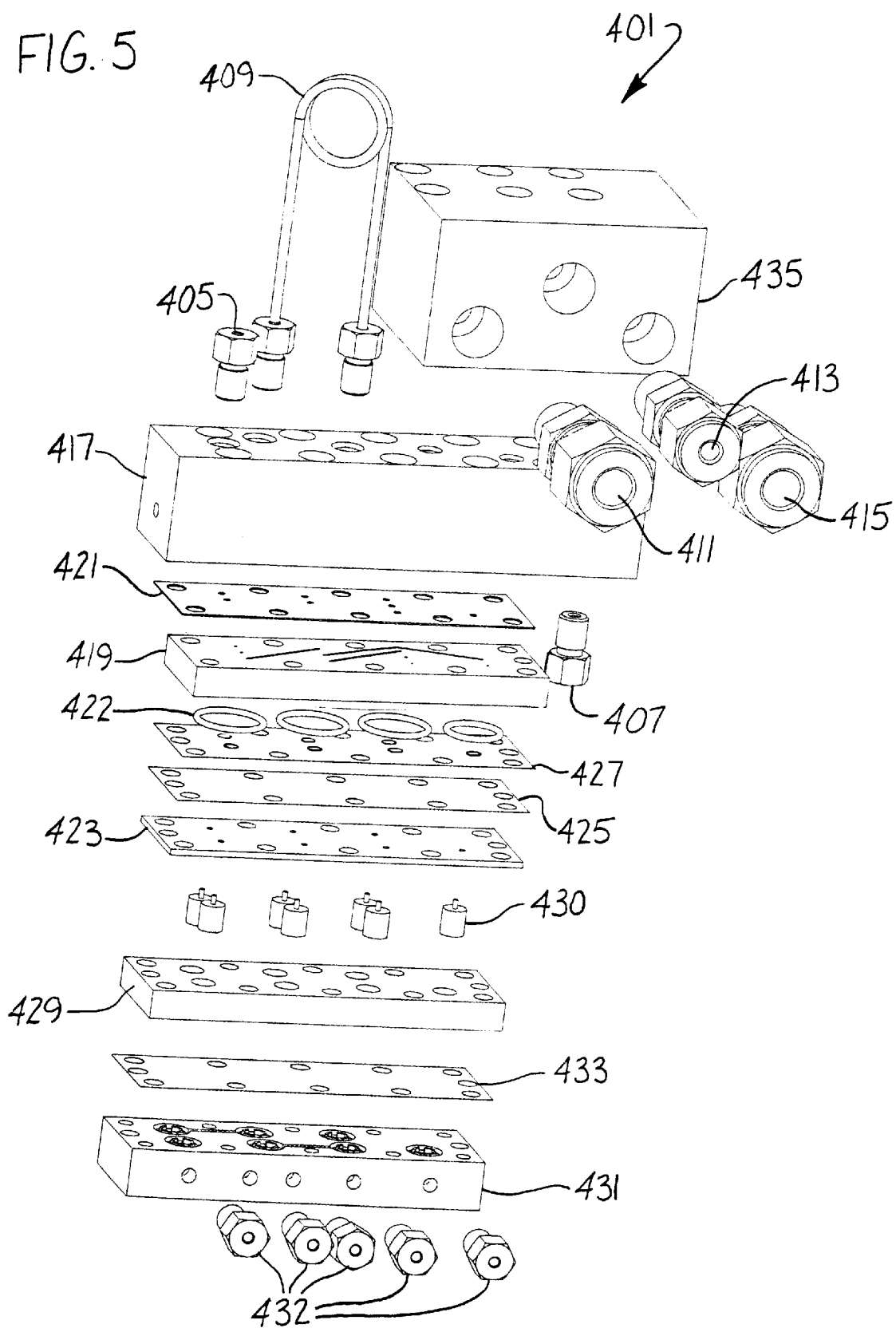

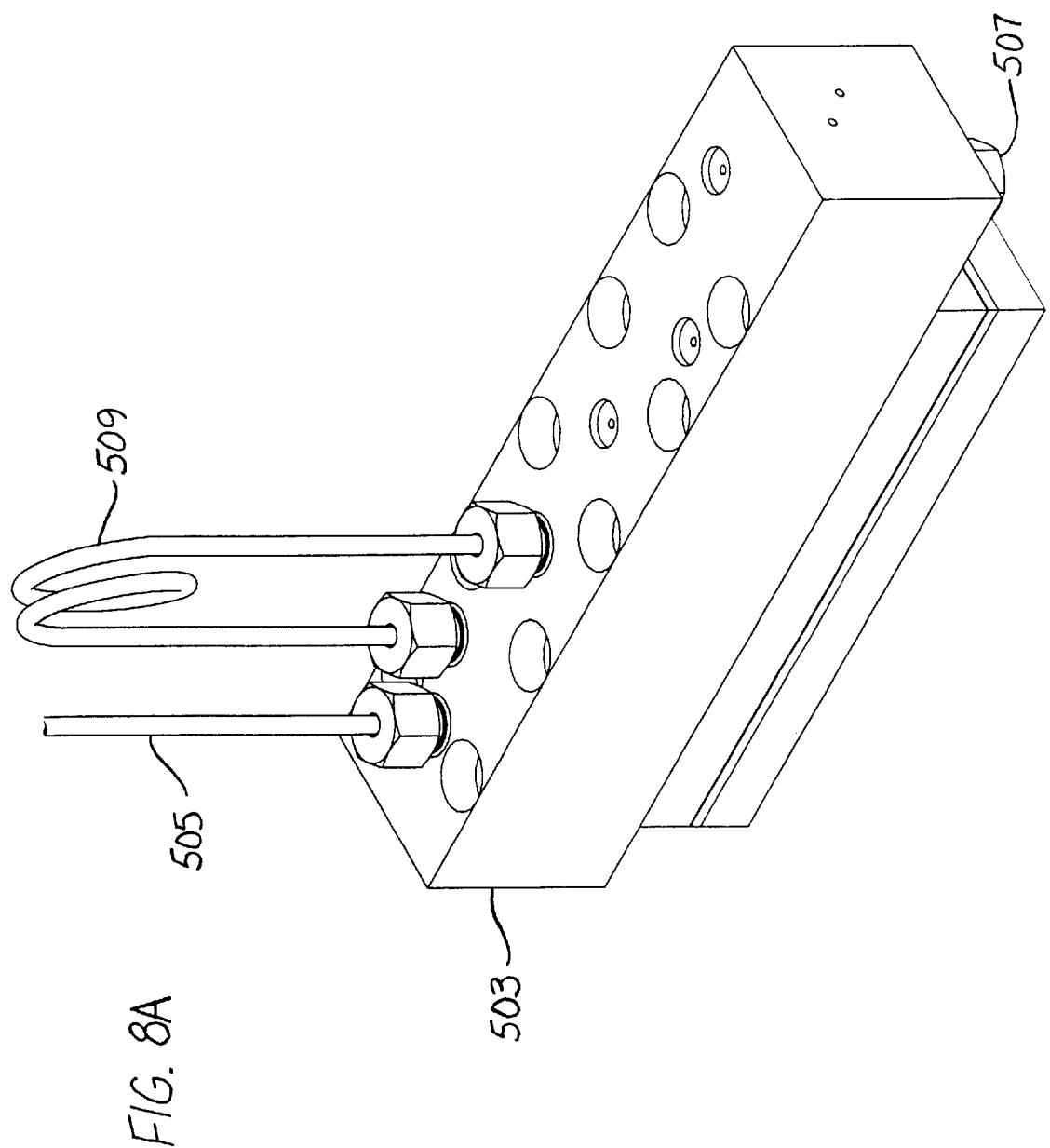

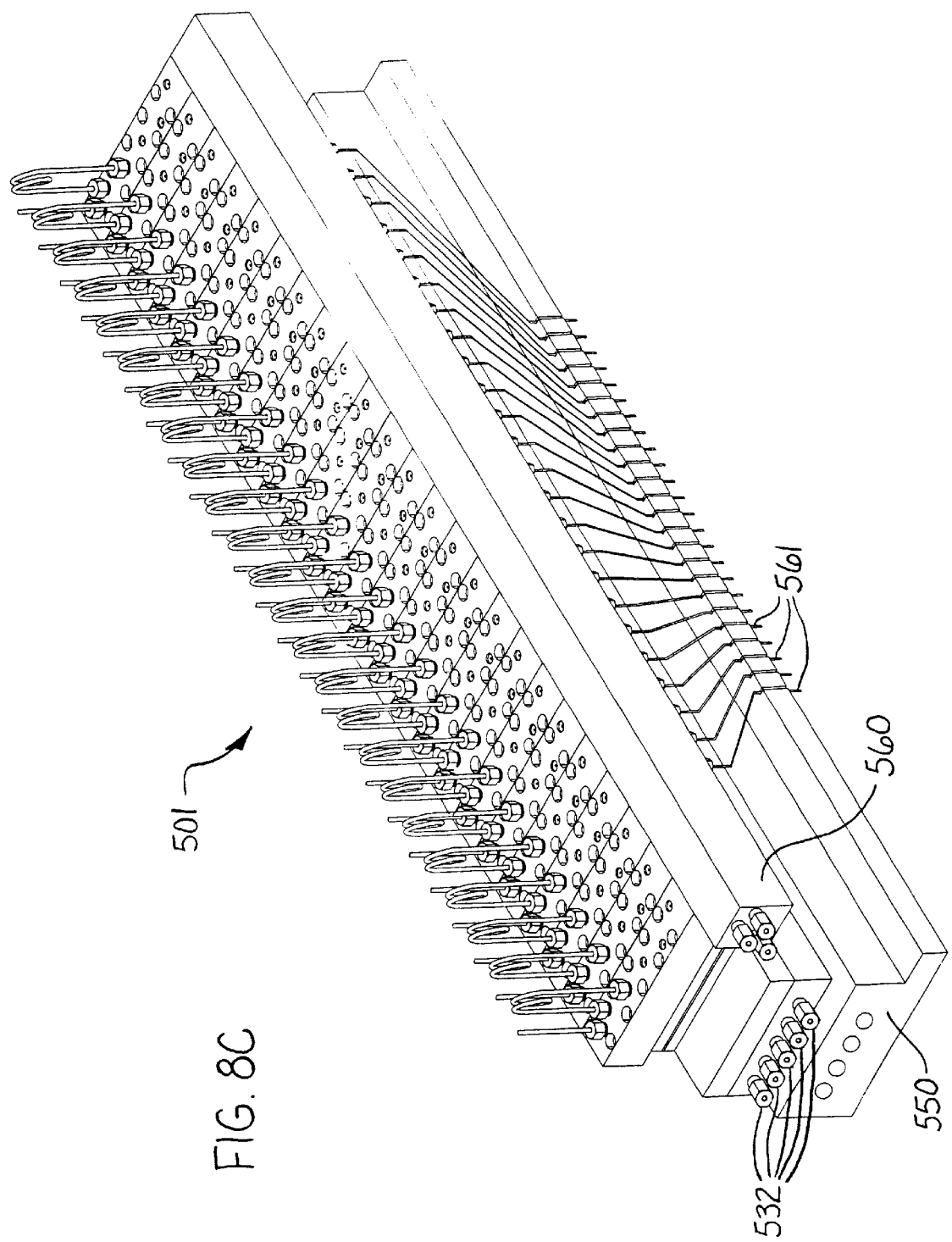

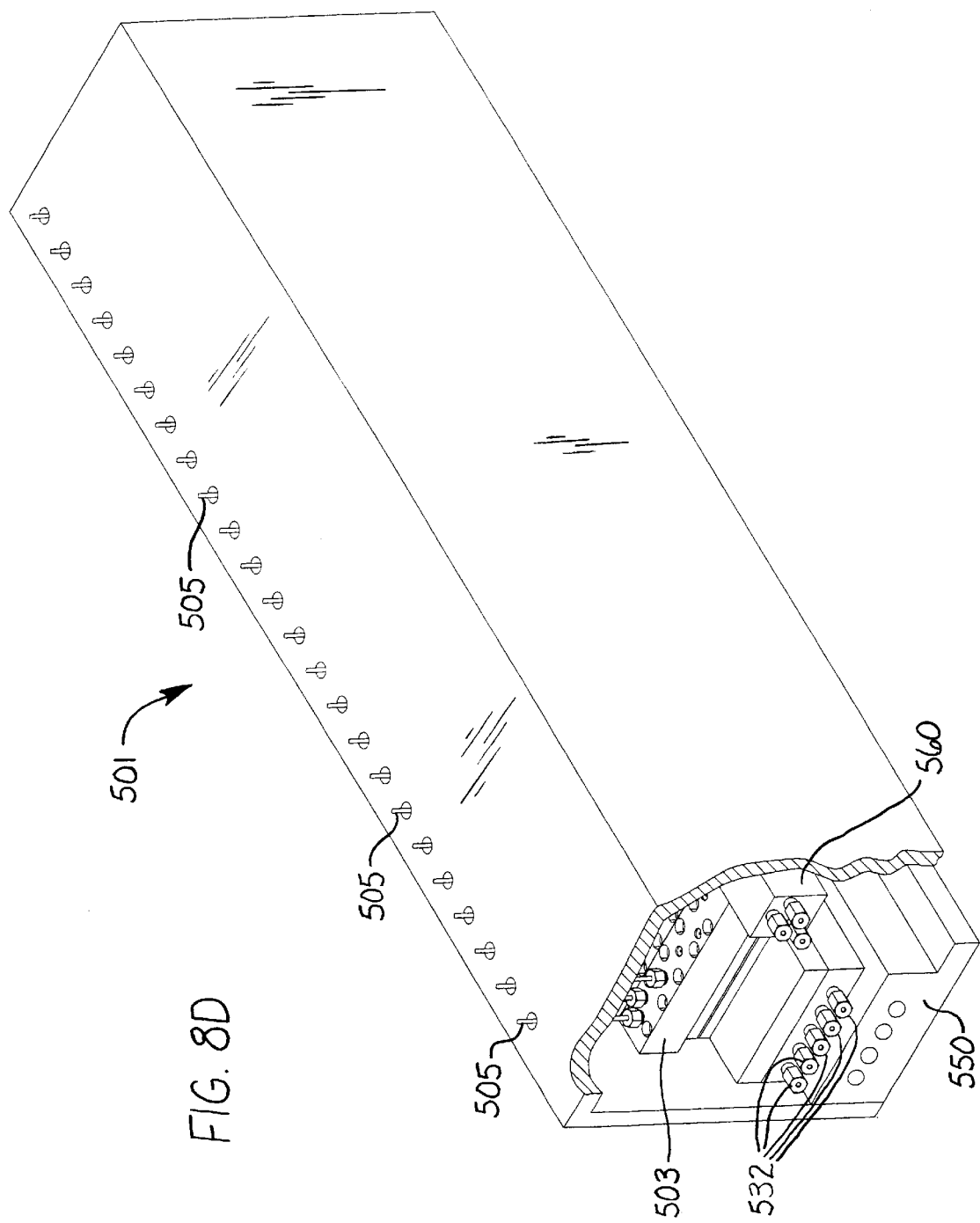

US 6,742,544 B2

INJECTION VALVE ARRAY

CROSS-REFERENCE TO RELATED APPLICATIONS

This application claims priority from U.S. Provisional Patent Application Serial No. 60/274,022, filed Mar. 7, 2001. The entire text of U.S. Provisional Application Serial No. 60/274,022 is hereby incorporated herein by reference.

BACKGROUND OF THE INVENTION

The present invention generally relates to a novel fluid control valve, more particularly an injection valve comprising a plurality of microvalves for injecting discrete charges of gas into a mobile phase or carrier stream, which is particularly useful in high resolution gas chromatography. Further, the present invention provides for parallel arrays of gas injection valves in which multiple samples may be injected into multiple carrier streams substantially simultaneously.

The parallel injection valves of the present invention can be advantageously incorporated into parallel detection systems, including especially parallel gas chromatographs. In a preferred application, the parallel injection valves can be used in conjunction with a multi-channel gas chromatograph as disclosed in U.S. Ser. No. 09/801,430, entitled "Parallel Gas Chromatograph with Microdetector Array" filed Mar. 7, 2001 by Srinivasan et al.

Such parallel detection systems are of substantial importance for high-throughput combinatorial catalysis research programs, wherein chemical reactions are conducted simultaneously using small volumes of reaction materials to efficiently and economically screen large libraries of chemical materials. Preferred parallel screening reactors include the parallel flow reactors as disclosed in U.S. Pat. No. 6,149,882 to Guan et al., U.S. Ser. No. 09/518,794 filed Mar. 3, 2000 by Bergh et al., U.S. Ser. No. 60/185,566 filed Mar. 7, 2000 by Bergh et al., U.S. Ser. No. 60/229,984 filed Sep. 2, 2000 by Bergh et al., U.S. Ser. No. 09/801,390, entitled "Parallel Flow Process Optimization Reactor" filed Mar. 7, 2001 by Bergh et al., U.S. Ser. No. 09/801,389, entitled "Parallel Flow Reactor Having Variable Feed Composition" filed Mar. 7, 2001 by Bergh et al., and U.S. Ser. No. 60/274,065, entitled "Parallel Flow Reactor Having Improved Thermal Control" filed on Mar. 7, 2001 by Bergh et al. These reactors can effect reactions in tens, hundreds or even thousands of channels simultaneously or substantially concurrently.

In more advanced online gas monitoring applications such as the high-throughput combinatorial catalysis research programs described above, it is possible to produce sample streams of fluid at various pressures. Most often the samples are at a different pressure than the carrier stream of the gas chromatograph. Injecting samples into a carrier stream at a different pressure is undesirable as pressure gradients can cause sample dispersion, which results in unwanted band broadening that may detrimentally affect the quality of the analysis of the sample. Moreover, pressure difference between samples makes the sample sizes different. Thus, it is important to be able to depressurize the sample after collection, and before injection or transfer to an analysis system, to minimize band broadening and to ensure accurate, reliable analysis.

WO 00/23734 discloses a gas chromatography apparatus comprising a multi-valve assembly including a series of microvalves for sample injection. The multi-valve assembly comprises a series of plates and diaphragms wherein fluid flow is controlled by two pistons. A pressurized actuation gas operates to alternately elevate one or the other of the pistons, which acts to either open or close an individual microvalve. The disclosed multi-valve assembly incorporates six individual microvalves which operate in combination in the same way as a standard 6-port rotary injection valve known in the art of fluid control. Thus, the microvalves of the reference do not provide for sample depressurization prior to sample injection. Further, the rotary arrangement of the disclosed multi-valve assembly limits the size of the valve apparatus such that it is not compatible with or readily capable of being incorporated in a large, parallel chromatography array.

Unlike the prior art, the present invention discloses a gas injection valve comprising a plurality of novel microvalves that can be arranged in valving schemes relevant to online gas analysis applications, for example, allowing a discrete sample of a gas to be depressurized prior to transfer or injection into an analysis apparatus or reaction system.

SUMMARY OF THE INVENTION

Among the several objects and features of the present invention may be noted the provision of a gas injection valve comprising one or more microvalves; the provision of such an injection valve wherein each microvalve is capable of being independently actuated; the provision of such an injection valve that may be micro-fabricated; the provision of such an injection valve capable of receiving gas at different pressures and emitting discrete charges of gas at approximately the same pressure; and the provision of such an injection valve which may be incorporated into a parallel array of injection valves for handling multiple gas samples substantially simultaneously.

Briefly, therefore, apparatus of the invention is a microvalve assembly for use in receiving gas at different pressures and emitting discrete charges of gas at approximately the same pressure. The microvalve assembly comprises a valve body having a gas inlet passage adapted for connection to a line for receiving gas at different pressures, a gas outlet passage, a gas charge loop and a pressure control port. The microvalve assembly further comprises (1) a first microvalve associated with the valve body adapted to admit gas passing into the gas inlet passage into the gas charge loop in a first position of the valve and to block entry of gas from the gas inlet passage into the gas charge loop in a second position; (2) a second microvalve associated with the valve body adapted to open the gas charge loop to the pressure control port for reducing the pressure of gas in the gas charge loop in a first position and to block the gas charge loop from the pressure control port in a second position; and, (3) a third microvalve associated with the valve body adapted to open the gas charge loop to the gas outlet passage for emitting the discrete charge of gas from the gas loop from the valve body in a first position and to block the gas charge loop from the gas outlet passage in a second position.

Further, apparatus of the invention include an injection valve array capable of controlling fluid flow from multiple sources substantially simultaneously. The injection valve array comprises multiple injection valves arranged generally adjacent in a linear or curvilinear array. Each injection valve comprises at least one microvalve including (1) a first plate having inlet passages, outlet passages, and fluid transfer channels in a first face, the fluid transfer channels extending between respective pairs of inlet passages and outlet passages to permit fluid communication between the pairs of inlet and outlet passages of said first plate extending between the inlet and outlet passages for fluid communication therebetween; (2) a second plate in generally opposed relation with the first face of the first plate and having piston receptacles toward the first face of the first plate; (3) a sealing membrane located between the first face of the first plate and the second plate; and, (4) a piston for each of said piston receptacles of the second plate, each piston being at least partially disposed in the piston receptacle and movable relative to the first plate between an open position in which the sealing membrane does not block fluid flow in a corresponding one of the fluid transfer channels between the inlet passage and outlet passage, and a closed position in which the piston deforms the sealing membrane to block fluid flow in said corresponding one of the fluid transfer channels between the inlet passage and outlet passage.

Further, apparatus of the invention include a gas injection valve for use in injecting gas samples at controlled pressure into a gas chromatograph. The gas injection valve comprises a gas sample inlet port; a carrier gas inlet port; a gas sample loop; a waste port; a pressure control port; an outlet port; passaging extending between the gas sample inlet port, the carrier gas inlet port, the gas sample loop, the waste port, the pressure control port and the outlet port; and microvalves at least partially disposed in said passaging for selectively blocking the flow of gas between the gas sample inlet port, the carrier gas inlet port, the gas sample loop, the waste port, the pressure control port and the outlet port except through the microvalves. The microvalves are operable to (1) a first state in which the gas sample inlet port is in fluid communication with the sample loop and the waste port, and the carrier gas inlet port is in fluid communication with the outlet port, (2) a second state in which the gas sample loop is blocked from the gas sample inlet port and in fluid communication with the pressure control port for controlling the pressure of the gas in the gas sample loop, the gas sample inlet port is in fluid communication with the waste port, and the carrier gas inlet port remains in fluid communication with the outlet port, and (3) a third state in which the carrier gas inlet port is in fluid communication with the gas sample loop and the gas sample loop is in fluid communication with the outlet port for injecting the gas in the gas sample loop out of the valve through the outlet port.

Still further, apparatus of the invention includes a parallel injection valve for simultaneously injecting each of four or more gas samples into a mobile phase for fluid communication with one of four or more gas chromatography columns of a gas chromatograph. The parallel injection valve comprises four or more microvalve assemblies, each of the four or more microvalve assemblies being adapted to receive one of the four or more samples into a sample loop at a first pressure, to change the pressure of the sample to a second pressure while the sample resides in the sample loop, and to discharge the changed-pressure sample into the mobile phase.

Still further, the invention is directed to a combinatorial chemistry reaction and evaluation system. The system comprises (1) a reactor including multiple reaction chambers adapted for receiving inputs and creating reaction product gas samples at different pressures; (2) an array of injection valves connected to the reactor for receiving the gas samples at different pressures, the injection valves each being adapted to segregate a discrete sample of gas, control the pressure of the sample and emit the discrete gas sample; and, (3) a gas chromatograph having multiple sample columns and a detection system comprising four or more flow detectors, the gas chromatograph being connected to the injection valve array for receiving parallel discrete samples from the injection valve array and analyzing the composition of the samples in parallel.

Still further, the invention is directed to a method of injecting discrete gas samples at a controlled pressure to a gas chromatograph for analysis. The method comprises receiving sample gas to be analyzed into an injection valve; feeding the received sample gas through a sample loop; isolating the sample loop from receiving further sample gas; controlling the pressure of the gas in the sample loop; and injecting the controlled pressure sample gas in the sample loop into the gas chromatograph.

Other objects and features of the present invention will be in part apparent and in part pointed out hereinafter.

BRIEF DESCRIPTION OF THE DRAWINGS

FIG. 3A is a schematic vertical cross section of a second embodiment of the present invention, wherein all of the microvalves of the injection valve are in an open position;

FIG. 3B is a schematic vertical cross section similar to FIG. 3A except that one of the microvalves of the injection valve is in a closed position;

FIG. 5 is an exploded perspective view of the third embodiment of the present invention having the individual plates of the injection valve separated to illustrate their construction;

Corresponding reference characters indicate corresponding parts throughout the several views of the drawings.

DETAILED DESCRIPTION OF THE PREFERRED EMBODIMENTS

The present invention provides a novel gas injection valve comprising one or more microvalves for injecting discrete gas samples ("plugs") of a predetermined size (e.g., volume, mass) into a carrier stream, for example, a mobile phase in fluid communication with an apparatus for flow measurement, screening or analysis such as a high resolution gas chromatograph or a mass spectrometer. For the purposes of the present invention, the term "gas injection valve" or "injection valve" refers to an apparatus for injecting a single sample stream into a mobile phase. The terms "gas injection valve" and "injection valve" are used interchangeably with the term "microvalve assembly" to indicate that the apparatus operating on a single sample stream may comprise one or more microvalves. As used herein, the term "microvalve" is meant to have its ordinary meaning in the art of fluid control, particularly referring to a fluid control device whose critical features are less than about 0.5 cm in size and may more typically have a size ranging from about a micron to about a millimeter. Critical features may include the membrane thickness, passage sizes, the size of the valve seats, etc. Further, the terms "parallel injection valve" and "injection valve array" as used interchangeably herein, refer to a combination of injection valves generally arranged side by side in a linear or curvilinear array which are capable of injecting multiple gas samples into multiple carrier streams substantially simultaneously.

In preferred embodiments, injection valves of the present invention accommodate a plurality of microvalves arranged in a variety of valving schemes. For example, in a particularly preferred injection valve of the present invention, multiple microvalves are employed in a valving scheme in which gas samples are collected at different pressures, for example, at pressures above that of the carrier stream. The samples having higher pressures are depressurized prior to injection into the carrier stream. Depressurizing gas samples prior to transfer to a carrier stream for injection into a flow detection, screening or analysis apparatus is important, particularly in high resolution gas chromatography, to minimize sample dispersion in the carrier gas, which may result in band broadening during sample analysis. Further, depressurizing the gas sample ensures that sample size (e.g., volume, mass) may be adequately controlled, which is often difficult when sampling gases at different pressures. Thus, the valving arrangements provided for in the present invention are particularly relevant to online gas analysis operations, for example, parallel screening reactors and parallel detection systems as employed in high-throughput combinatorial catalysis research programs.

Figure 1:
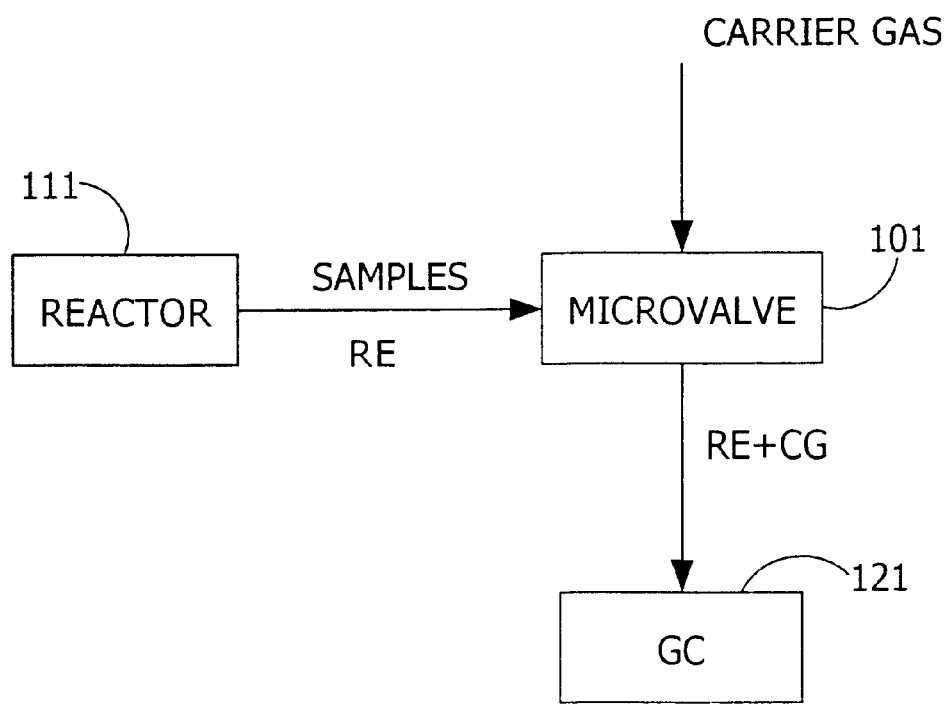
FIG. 1 is a diagrammatic view of an online gas analysis system including an injection valve of the present invention.

Referring now to the drawings, an injection valve of the present invention is generally indicated at 101 in FIG. 1. The injection valve 101 is particularly useful for transferring gas samples from a parallel pressure reactor 111 to an online gas analysis apparatus 121, particularly a parallel gas chromatograph as employed in high-throughput combinatorial catalysis research applications. As illustrated in the flow diagram, gas samples or reactor effluent ("RE") generated in the parallel reactor 111 is injected into a carrier gas ("CG") by the injection valve 101 for transfer to the online flow analysis apparatus 121, which is most preferably a high resolution gas chromatograph or a mass spectrometer. Although the present invention is described throughout the specification and shown in FIG. 1 as operating in a parallel gas chromatography system, it is important to note that an injection valve of the present invention can likewise be employed in any system for handling small, discrete quantities of fluid. For example, it is contemplated that an additional injection valve of the present invention may be incorporated into the parallel gas chromatography system of FIG. 1 as a fluid control device for pulse feeding reactants into the parallel reactor 111.

Figure 2A:
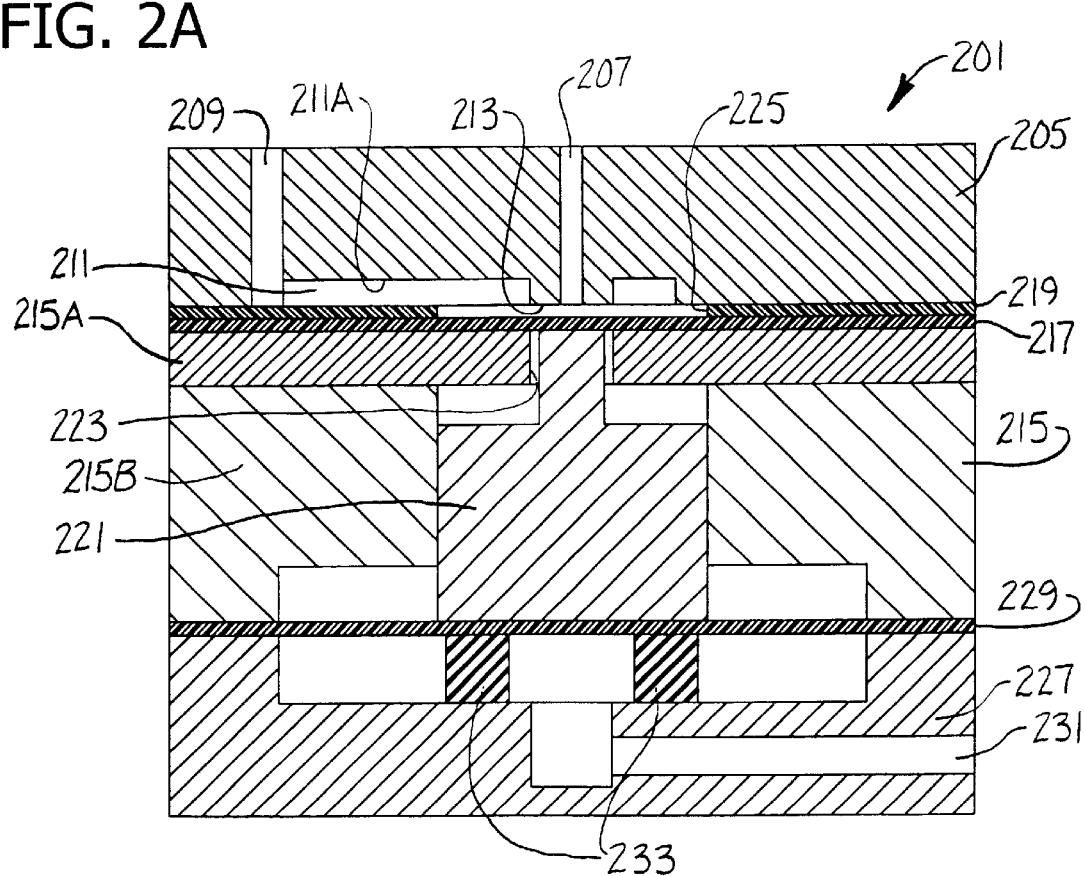
FIG. 2A is a schematic vertical cross section of a first embodiment of the injection valve of the present invention showing a microvalve in a first, open position.
Figure 2B:
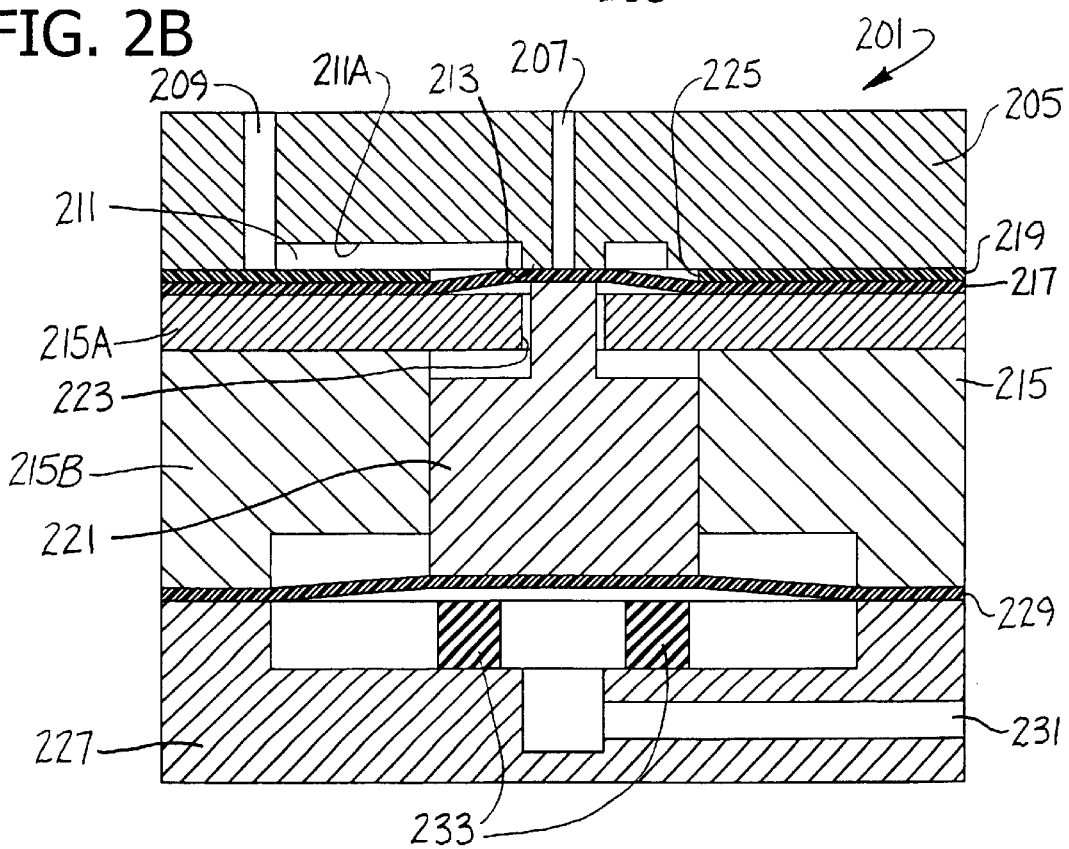
FIG. 2B is a schematic vertical cross section similar to FIG. 2A but showing the microvalve in a second, closed position.
Figure 2C:
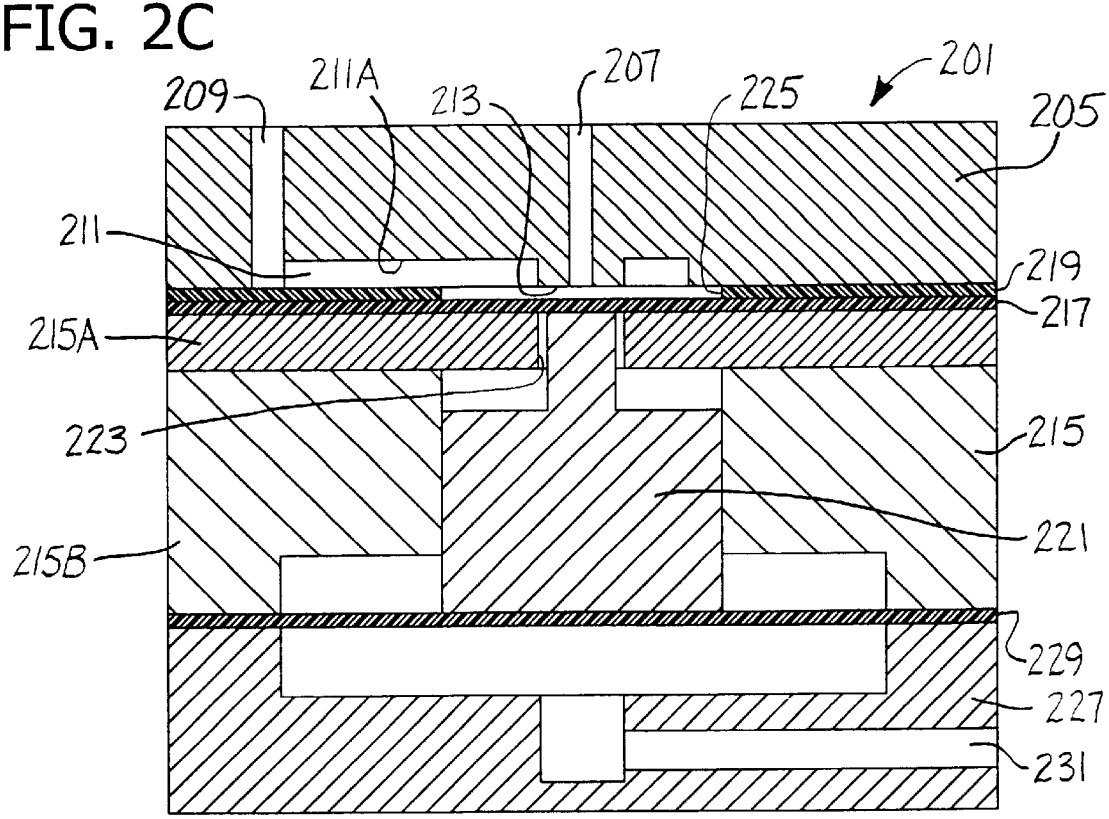
FIG. 2C is a schematic vertical cross section similar to FIG. 2A except that the injection valve does not have a stopper in the third plate.
Figure 2D:
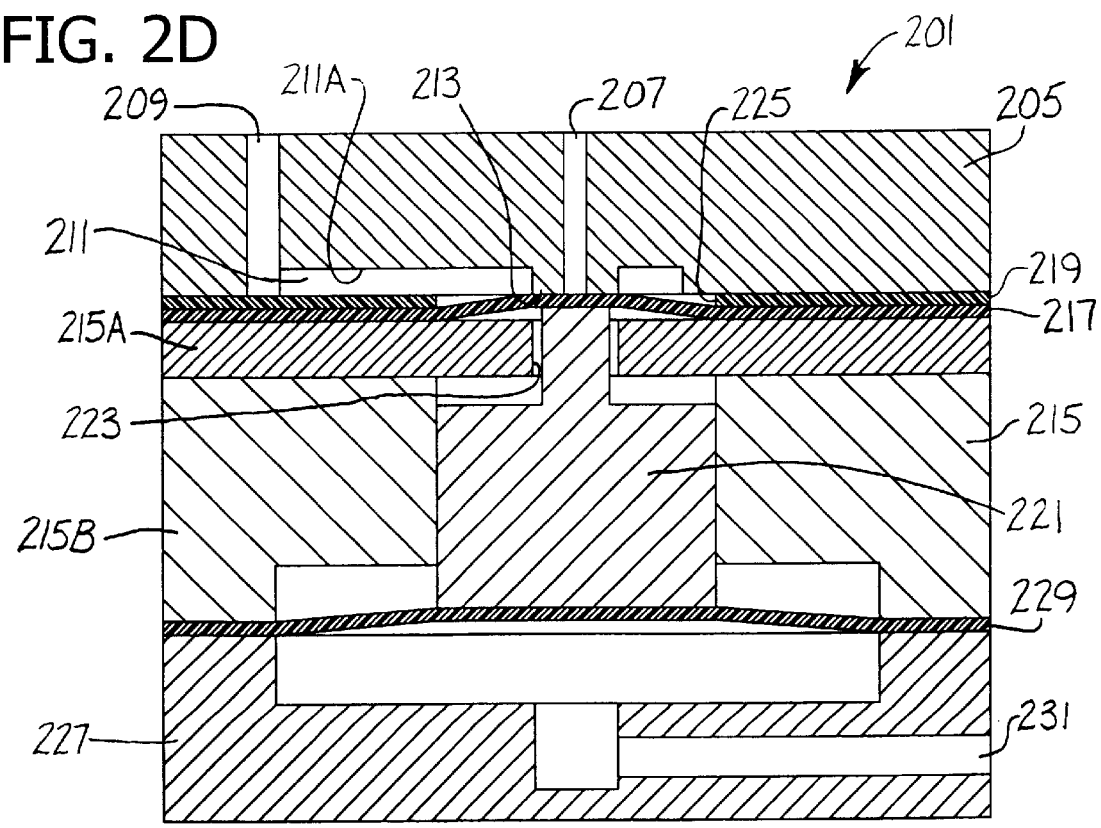
FIG. 2D is a schematic vertical cross section similar to FIG. 2B except that the injection valve does not have a stopper in the third plate.

Referring to FIGS. 2A and 2B, in a first embodiment, an injection valve 201 of the present invention comprises a single microvalve. It is important to note that the injection valve of the present invention includes a top plate (not shown in the schematic diagrams of FIGS. 2A and 2B) that will be fully described herein in relation to FIG. 5.

Referring back to FIGS. 2A and 2B, microvalve 201 generally comprises a first plate 205 having an inlet passage 207, an outlet passage 209 and a fluid transfer channel 211. The inlet passage 207 and outlet passage 209 extend through the first plate 205 from a first face to a second face. The fluid transfer channel 211 formed in the first face of the first plate 205 has a floor 211A and extends between the inlet passage 207 and outlet passage 209 of the first plate 205 for fluid communication therebetween.

The microvalve 203 further comprises a valve seat 213, a second plate 215, a sealing membrane 217, a spacer membrane 219 and a piston 221. In the illustrated embodiment, the second plate includes two plate members 215A, 215B. The valve seat 213 extends outwardly from the floor 211A of the fluid transfer channel 211 toward the first face of the first plate 205. Second plate 215 is positioned in generally opposed relation with the first face of the first plate 205 and has a piston receptacle 223 opening from the second plate 215 toward the first face of the first plate 205. The sealing membrane 217 is located between the first face of the first plate 205 and the second plate 215. Piston 221 is at least partially disposed in the piston receptacle 223 of the second plate 215.

Spacer membrane 219 is located between the sealing membrane 217 and the first face of the first plate 205 for spacing the sealing membrane from the first face of the first plate. The spacer membrane 219 has an opening 225 therein generally aligned with the valve seat 213 whereby the sealing membrane 217 may be deformed through the opening by movement of the piston 221 and into engagement with the valve seat to seal the inlet passage 207 from fluid communication with the fluid transfer channel 211. Preferably, the spacer membrane 219 sealingly engages the first face of the first plate 205 over the fluid transfer channel 211 except at the opening 225 of the spacer membrane 219. Thus, fluid in the fluid transfer channel 211 can flow only between the inlet and outlet passages 207, 209.

The microvalve 201 still further comprises a third plate 227 and an actuation membrane 229. Third plate 227 is in generally opposed relation with the second plate 215 on the opposite side of the second plate from the first plate 205. The third plate 227 has a fluid activation passage 231 therein opening from the third plate 227 toward the second plate 215 and associated with piston receptacle 223. Actuation membrane 229 is disposed between the third plate 227 and the second plate 215 and closes the fluid activation passage opening. The actuation membrane 229 is deformable in a region of the fluid activation passage opening upon application of fluid pressure to said passage to engage the piston 221 for moving the piston. Preferably, third plate 227 additionally includes a stopper 233 positioned in the area of the fluid activation passage opening to restrict the range of movement of the piston for minimizing plastic deformation of the actuation membrane 229.

The microvalve 201 operates by moving the piston 221 relative to the first plate 205 between an open position (FIG. 2A) in which the sealing membrane 217 is spaced apart from the valve seat 213 to permit fluid flow between the inlet passage 207 and outlet passage 209 through the fluid transfer channel 211, and a closed position (FIG. 2B) in which the piston 221 presses the sealing membrane 217 against the valve seat 213 to prevent fluid flow between the inlet passage 207 and the outlet passage 209 through the fluid transfer channel 211.

The microvalve 201 is operated by an actuator (not shown) in fluid communication with fluid activation passage 231. The actuator supplies pressurized fluid, preferably a pressurized actuation gas, which acts on actuation membrane 229 via fluid activation passage 231. In the open position of the microvalve as described above, no pressurized fluid is supplied by the actuator and the actuation membrane 229 is in its relaxed position (FIG. 2A). To close the microvalve as described above, pressurized fluid supplied by the actuator via fluid activation passage 231 acts to deform the actuation membrane 229 from its normal position to move the piston 221 into the closed position as described above and as shown in FIG. 2B.

The injection valve of the present invention may be constructed in any geometrical arrangement, for example, curved, circular or linear, with linear arrangements being generally more preferred to achieve greater spatial density. Preferably, each injection valve has a rectangular outer profile in plan to facilitate closely packing the valves together. However the arrangement, the first face of the first plate 205 preferably lies generally in a plane and the valve seat 213 includes an engagement surface (contacted by the sealing membrane 217 in the closed position) lying generally in the plane of the first face.

Microvalves of the injection valves and injection valve arrays of the present invention can be fabricated by methods known in the art. See, for example, Rich et al., "An 8-Bit Microflow Controller Using Pneumatically-Actuated Valves", pp. 130–134, IEEE (1999); Wang et al., "A Parylene Micro Check Valve", pp. 177–182, IEEE (1999); Xdeblick et al., "Thermpneumatically Actuated Microvalves and Integrated Electro-Fluidic Circuits", 251–255, TRF, Solid State Sensor and Actuator Workshop, Hilton Head, S.C., Jun. 13–16 (1994); and Grosjean et al., "A Practical Thermpneumatic Valve", 147–152, IEEE (1999). As will be apparent to one skilled in the art, injection valves of the present invention may be constructed of any materials that are capable of being precision machined or microfabricated. Suitable materials include, for example, metal, glass, silicon, ceramic or quartz. In a preferred embodiment, the injection valve comprises precision-machined stainless steel.

Membranes suitable for use in the invention may generally include polymer or metal films selected so as to minimize plastic deformation. Particularly preferred membranes include polyimide polymer films such as Kapton® commercially available from DuPont High Performance Films, Circleville, Ohio; teflon-coated polyimide polymer films; and fluoropolymer films such as Kalrez® commercially available from DuPont Dow Elastomers, Wilmington, Del.

Referring now to FIGS. 3A and 3B, in a second embodiment of the present invention, an injection valve 301 is provided having a plurality of microvalves generally indicated at 303 therein. Each microvalve is substantially similar to the microvalve of the first embodiment described above. Like the injection valve of the first embodiment, the second embodiment illustrated in the schematic drawings of FIGS. 3A and 3B has a top plate which is not shown. As above, the top plate will be fully described in relation to the later embodiments of the invention, particularly in regard to FIG. 5.

Referring back to FIGS. 3A and 3B, injection valve 301 comprises a first plate 305 having inlet passages 307, outlet passages 309, and fluid transfer channels 311 in a first face. The inlet passages 307 and outlet passages 309 extend through the first plate 305 from a first face to a second face. The fluid transfer channels 311 have a floor 311A and extend between respective pairs of inlet passages 307 and outlet passages 309 to permit fluid communication therebetween.

Injection valve 301 further comprises valve seats 313, a second plate 315, a sealing membrane 317, a spacer membrane 319 and pistons 321. In the illustrated embodiment, the second plate 315 comprises two plate members 315A, 315B. The valve seats 313 extend outwardly from the floor 311A of the fluid transfer channels 311 toward the first face of the first plate 305. Second plate 315 is positioned in generally opposed relation with the first face of the first plate 305 and has a plurality of piston receptacles 323 opening from the second plate 315 toward the first face of the first plate 305. The sealing membrane 317 is located between the first face of the first plate 305 and the second plate 315. Pistons 321 are at least partially disposed in the piston receptacles 323 of the second plate 315.

Spacer membrane 319 is located between sealing membrane 317 and the first face of first plate 305 for spacing the sealing membrane from the first face of the first plate. The spacer membrane has openings 325 therein generally aligned with the valve seats 313 whereby the sealing membrane may be deformed through the openings by movement of the pistons 321 and into engagement with the valve seats to seal the inlet passages 307 from fluid communication with the fluid transfer channels 311. Preferably, the spacer membrane sealingly engages the first face of the first plate over the fluid transfer channels except at the openings of the spacer membrane. Thus, fluid in the fluid transfer channels 311 can flow only between the corresponding pairs of inlet and outlet passages 307, 309.

The injection valve 301 still further comprises a third plate 327 and an actuation membrane 329. Third plate 327 is in generally opposed relation with the second plate 315 on the opposite side of the second plate from the first plate 305. Fluid activation passages 331 open from the third plate 327 toward the second plate 315 and are associated with the piston receptacles 323. Actuation membrane 329 is disposed between the third plate 327 and the second plate 315 to close the openings of the fluid activation passages 331. The actuation membrane 329 is deformable in a region of each fluid activation passage opening 331 upon application of fluid pressure to each fluid activation passage to engage one of the pistons 321 for moving the piston.

The injection valve 301 operates by moving the pistons 321 relative to the first plate 305 between an open position (FIG. 3A) in which the sealing membrane 317 is spaced from the valve seat 313 to permit fluid flow between the inlet passages 307 and outlet passages 309 through the fluid transfer channels 311, and a closed position in which the pistons 321 press the sealing membrane 317 against the valve seats 313 to prevent fluid flow between the inlet passages 307 and the outlet passages 309 through the fluid transfer channels 311. Each piston 321 is at least partially disposed in the piston receptacle 323 and movable relative to the first plate 305 between its open position (FIG. 3A) and its closed position.

The injection valve 301 is operated by one or more actuator(s) (not shown) in fluid communication with the fluid activation passages 331. Although the microvalves 303 of the injection valve 301 may be actuated in any combination (i.e., individually or in any combination), it is preferred that at least some of the microvalves 303 are independently actuated to allow for flexibility in designing valving schemes within the injection valve 301. Thus, at least some of the pistons 321 are adapted for actuation independently of the other pistons 321 within the injection valve. As shown in FIG. 3B, one of the microvalves is closed while the other remains open. The actuator(s) (not shown) supply pressurized fluid, preferably a pressurized actuation gas, which acts on actuation membrane 329 via fluid activation passages 331. In the open position of one of the microvalves 303 as described above, no pressurized fluid is supplied by the actuator and the actuation membrane 329 is in its relaxed position (FIG. 3A). To close the microvalve 303, as described above, pressurized fluid supplied by the actuator via fluid activation passage 331 acts to deform the actuation membrane 329 from its relaxed position to move piston 321 into the closed position as described above and as shown in FIG. 3B.

Figure 4:
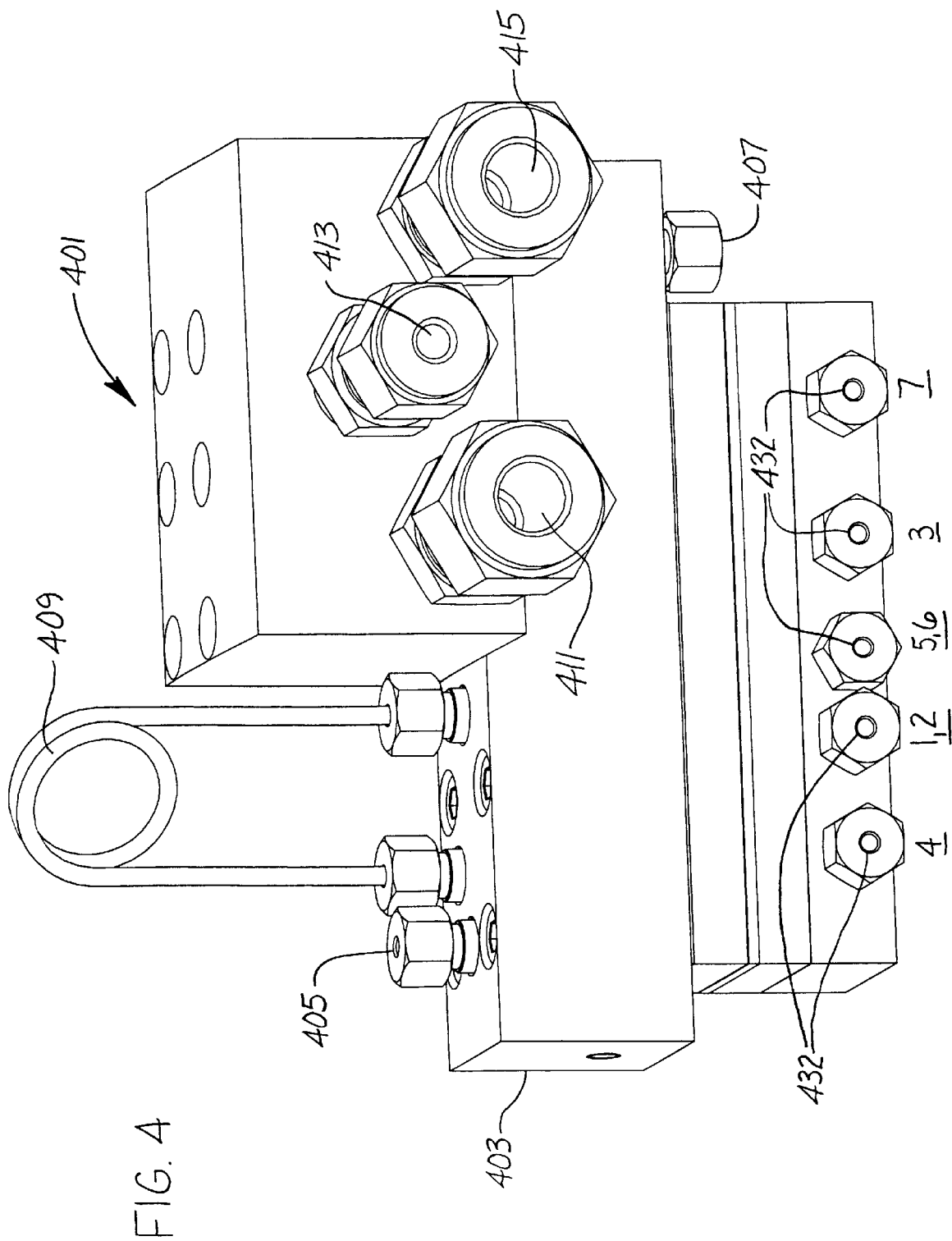
FIG. 4 is perspective view of a third, particularly preferred embodiment of an injection valve of the present invention.

In a third, particularly preferred embodiment, an injection valve of the present invention comprises seven microvalves configured to operate in a valving scheme particularly suited, for example, to online gas analysis systems. Referring now to FIG. 4, an injection valve of the present invention is illustrated at 401. The injection valve comprises a valve body 403 including a sample gas inlet passage 405 adapted for connection to a line for receiving gas at different pressures, a gas outlet passage 407, a gas sample loop 409 (broadly, "gas charge loop"), a carrier gas inlet passage 411 adapted for connection to a line for receiving a mobile phase, a waste outlet passage 413, a vent passage 415, and a plurality of fluid activation passages 432 adapted for connection to one or more actuators (not shown).

Referring now to FIG. 5, as illustrated in an exploded view of the valve body 403 shown in FIG. 4, gas injection valve 401 generally comprises a first plate 417 having a first face with fluid transfer channels therein, gas sample inlet passage 405, gas sample outlet passage 407 and gas sample loop 409; a second plate 419 in generally opposed relation with the first face of the first plate; a first sealing membrane 421 located between the first face of the first plate and the second plate; a third plate 423 in generally opposed relation with the second plate on the opposite side of the second plate from the first plate; a second sealing membrane 425 located between the second plate and the third plate; a sealing membrane 427 located between the second sealing membrane and the second plate for spacing the second sealing membrane from the second plate; one or more O-rings 422 located between the sealing membrane 427 and the second plate; a fourth plate 429 in generally opposed relation with the third plate on the opposite side of the third plate from the second plate and adapted for at least partially accomodating pistons 430; a fifth plate 431 in opposed relation to the fourth plate on the opposite side of the fourth plate from the third plate and having a plurality of fluid activation passages 432 adapted for connection to one or more actuators (not shown); and an actuation membrane 433 disposed between the fourth plate and the fifth plate.

Generally, first plate 417 includes portions of the gas sample inlet passage 405, gas sample outlet passage 407, gas sample loop 409, carrier gas inlet passage 411, waste outlet passage 413 and vent passage 415. Although not necessary or critical to the invention, it may be preferable in some arrangements, that the injection valve further include an end block as an adaptor for facilitating connections of the injection valve to other components of the system. For example, as shown in FIG. 5, end block 435 is provided as an adaptor in fluid communication with first plate 417 and contains carrier gas inlet passage 411, waste outlet passage 413 and vent passage 415. The second plate 419 contains other portions of the passages 405, 407, 409, 411, 413 and 415. The plate 419 is of substantial identical construction to plate 215, 315 of the prior embodiments. Essentially, the second plate 419 is acted on directly by the microvalves and the first plate provides for fluid transfer between microvalves and ultimate inlet and outlet ports.

Figure 6A:
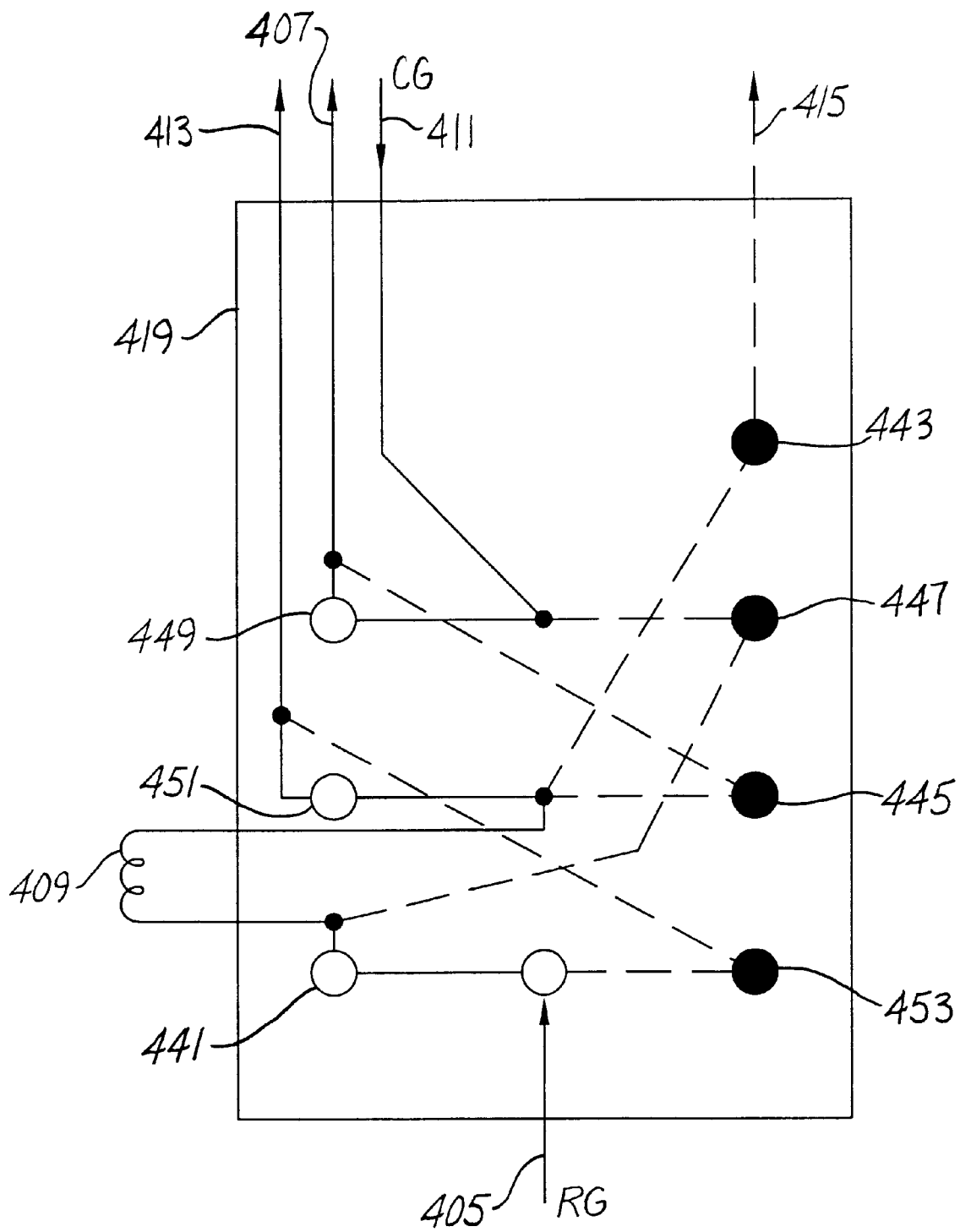
FIG. 6A is a schematic, horizontal cross section of the third embodiment of the present invention showing the microvalves and fluid transfer channels in a first face of the first plate of the injection valve with the injection valve in a first actuation state.
Figure 6B:
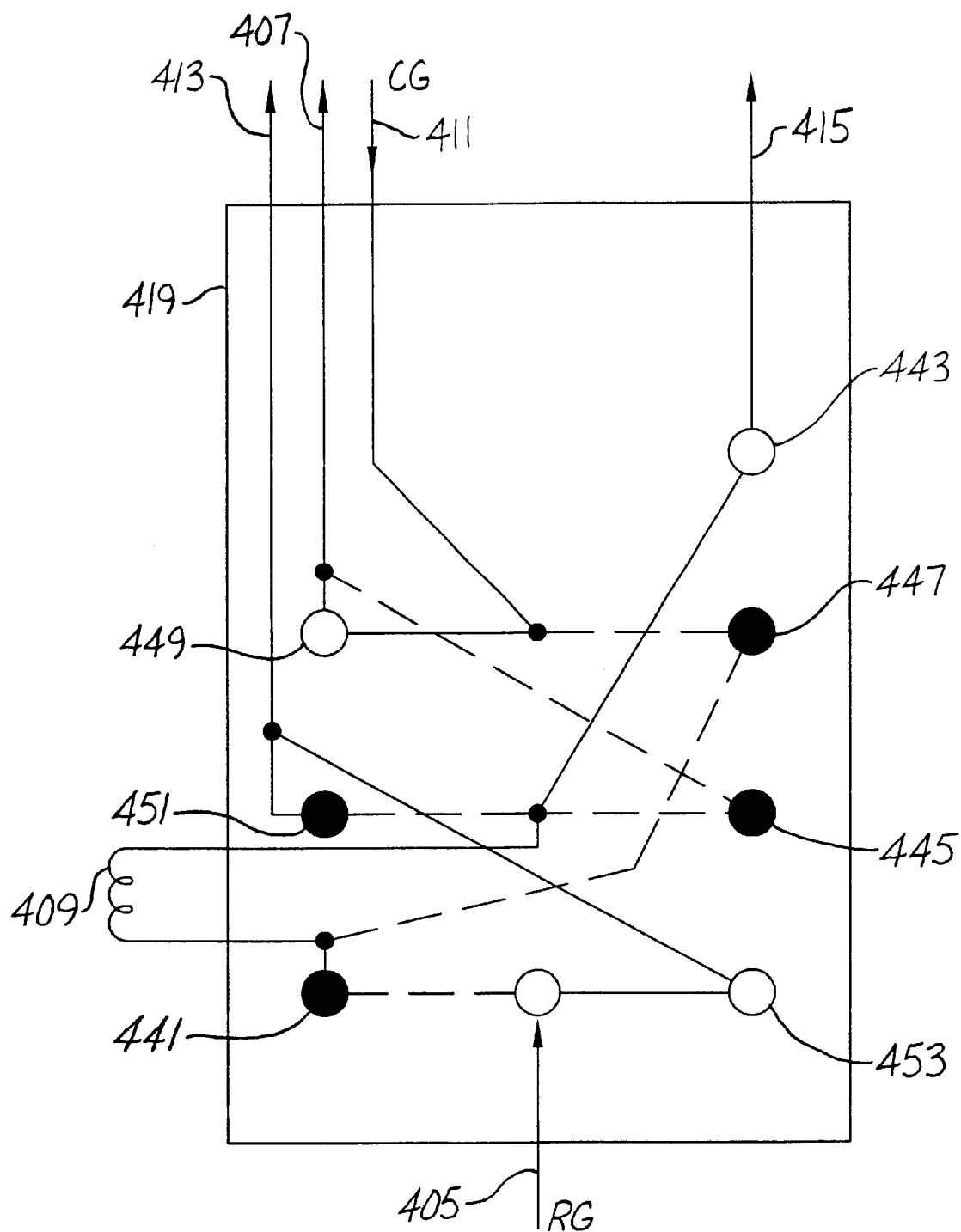
FIG. 6B is the schematic, horizontal cross section of FIG. 6A but showing the injection valve in a second actuation state.
Figure 6C:
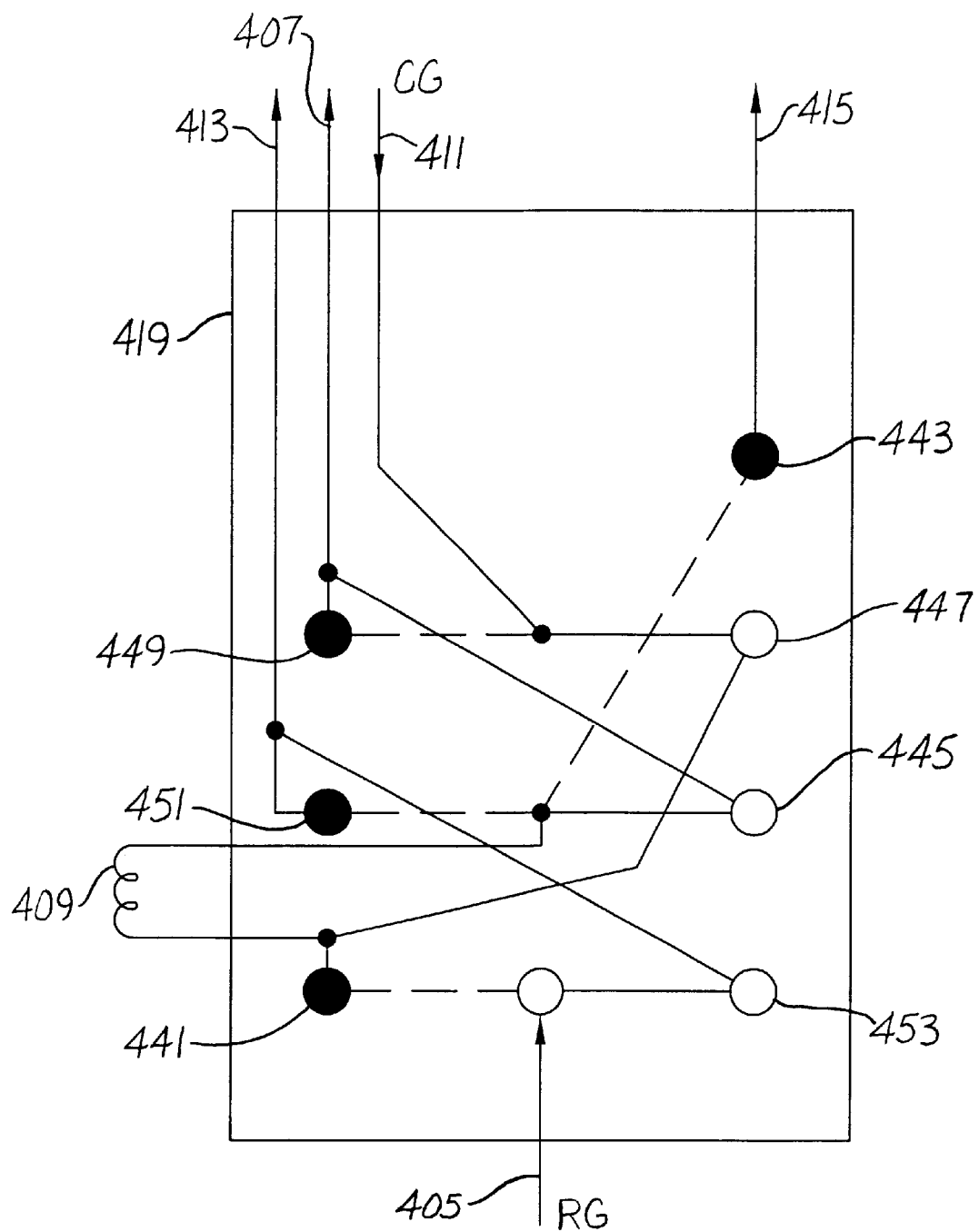
FIG. 6C is the schematic, horizontal cross section of FIG. 6A but showing the injection valve in a third actuation state.

Referring now to FIGS. 6A through 6C, the injection valve 401 is schematically illustrated from the vantage of the various fluid connections of the second plate 419. The injection valve 401 comprises seven microvalves including a first microvalve 441, a second microvalve 443, a third microvalve 445, a fourth microvalve 447, a fifth microvalve 449, a sixth microvalve 451 and a seventh microvalve 453. These microvalves have the same construction and operation as the microvalves of the first and second embodiments above. In the illustrated embodiment, microvalves 441–453 are located within the valve body 403. However, it is to be understood that the microvalves could be located substantially outside the valve body, such as valves having their own separate encasements mounted on a substrate containing connecting channels (not shown). The various interconnections of the valves are accomplished by passages through the second plate 419, channels formed in both faces of the second plate, tubing and passages in other plates of the valve 401. The formation and arrangement of these channels will be readily appreciated by those of ordinary skill in the art.

The first microvalve 441 is adapted to admit gas (i.e., reactant gas RG) passing into the gas inlet passage 405 into the gas sample loop 409 in a first, open position of the valve and to block entry of gas from the gas inlet passage 405 into the gas sample loop 409 in a second, closed position. The second microvalve 443 is adapted to open the gas sample loop 409 to the vent passage 415 for reducing the pressure of gas in the gas sample loop in a first position and to block the gas sample loop from the vent passage in a second position. In the embodiments described herein the vent passage 415 (broadly, "a pressure control port") vents gas in the gas sample loop to atmospheric pressure. However, it is to be understood that known pressure regulating devices may be employed to vent the gas in the loop to a reference pressure other than atmospheric. Moreover, available pressure control devices could be used to increase the pressure of the sample, if desired.

The third microvalve 445 is adapted to open the gas sample loop 409 to the gas outlet passage 407 for emitting the discrete charge of gas (i.e., the sample collected in the loop) from the gas loop out of the valve body 403 in a first position and to block the gas sample loop from the gas outlet passage in a second position. The fourth microvalve 447 is adapted to admit carrier gas from the carrier gas inlet passage 411 into the gas sample loop 409 in a first position when the third microvalve 445 is in a first position for pushing the gas in the gas sample loop out of the gas outlet passage 407 and to block flow of carrier gas into the gas sample loop in a second position.

The fifth microvalve 449 is adapted to permit flow of carrier gas directly from the carrier gas inlet passage 411 to the gas outlet passage 407 in a first position and to block carrier gas from the gas outlet passage in a second position. The sixth microvalve 451 is adapted to permit passage of gas in the gas sample loop 409 into the waste outlet passage 413 in a first position when the first valve is in the first position and to block flow of gas from the gas sample loop to the waste outlet passage in a second position. The seventh microvalve 453 is adapted to permit passage of gas in the sample gas inlet passage 405 into the waste outlet passage 413 in a first position when the first microvalve 441 is in the second position and to block flow of gas from sample gas inlet passage to the waste outlet passage in a second position.

Figure 7A:
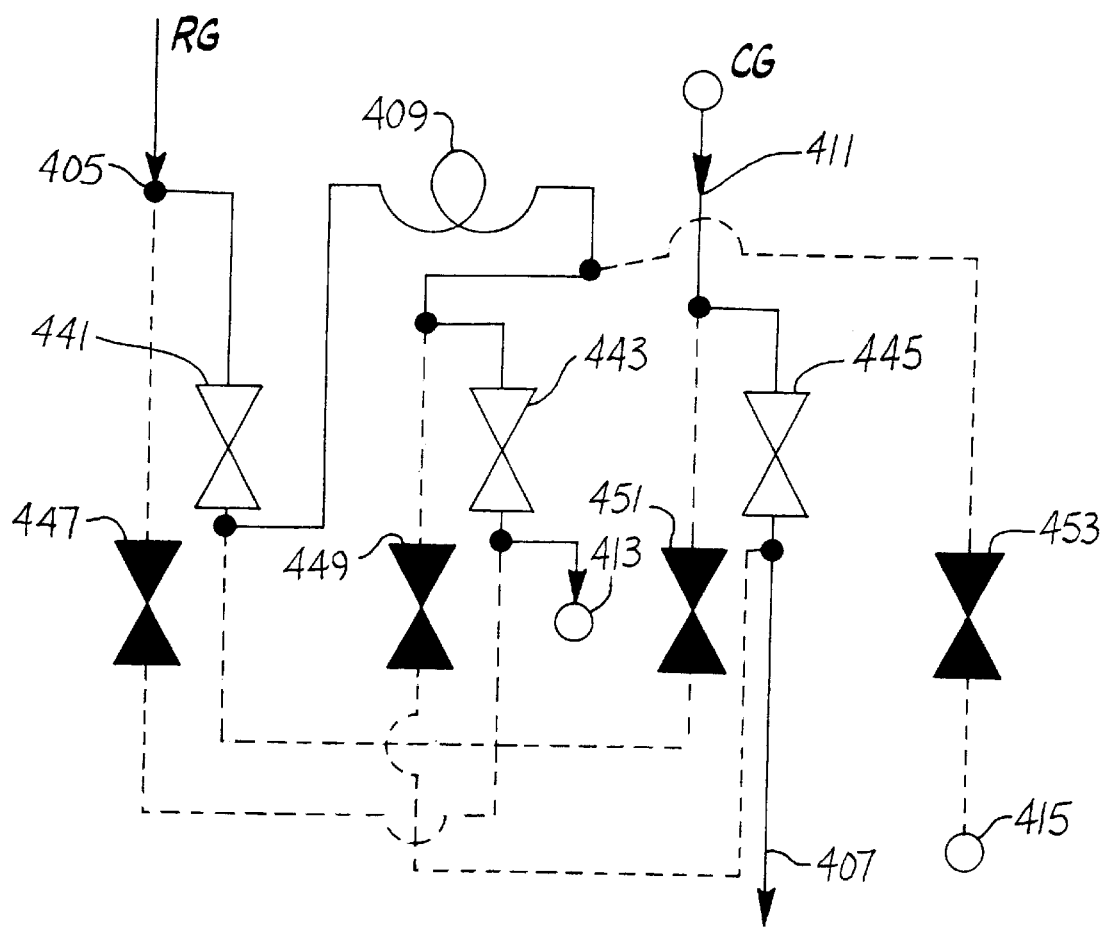
FIG. 7A is a diagrammatic representation of the third embodiment of the injection valve of the present invention showing the flow circuit of the injection valve in a first actuation state.
Figure 7B:
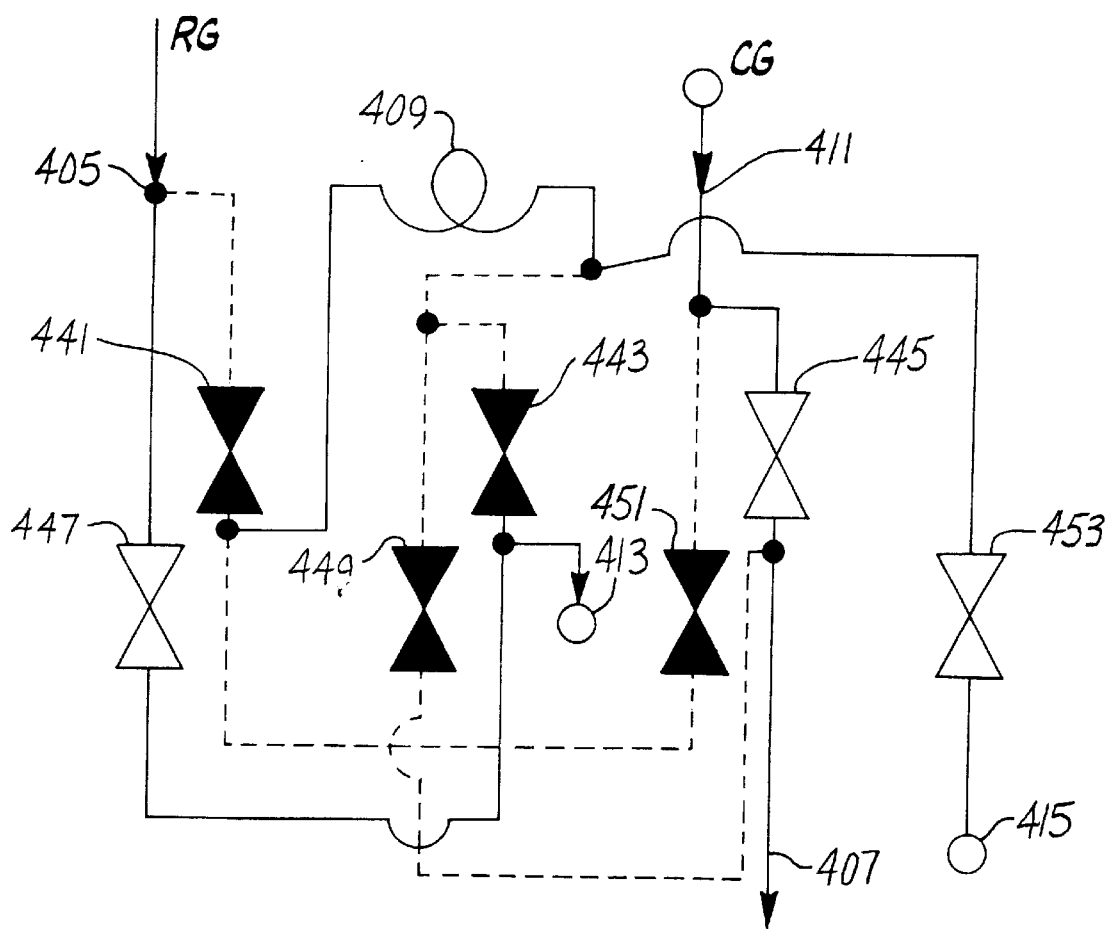
FIG. 7B is the diagrammatic representation of FIG. 7A but showing the flow circuit of the injection valve in a second actuation state.
Figure 7C:
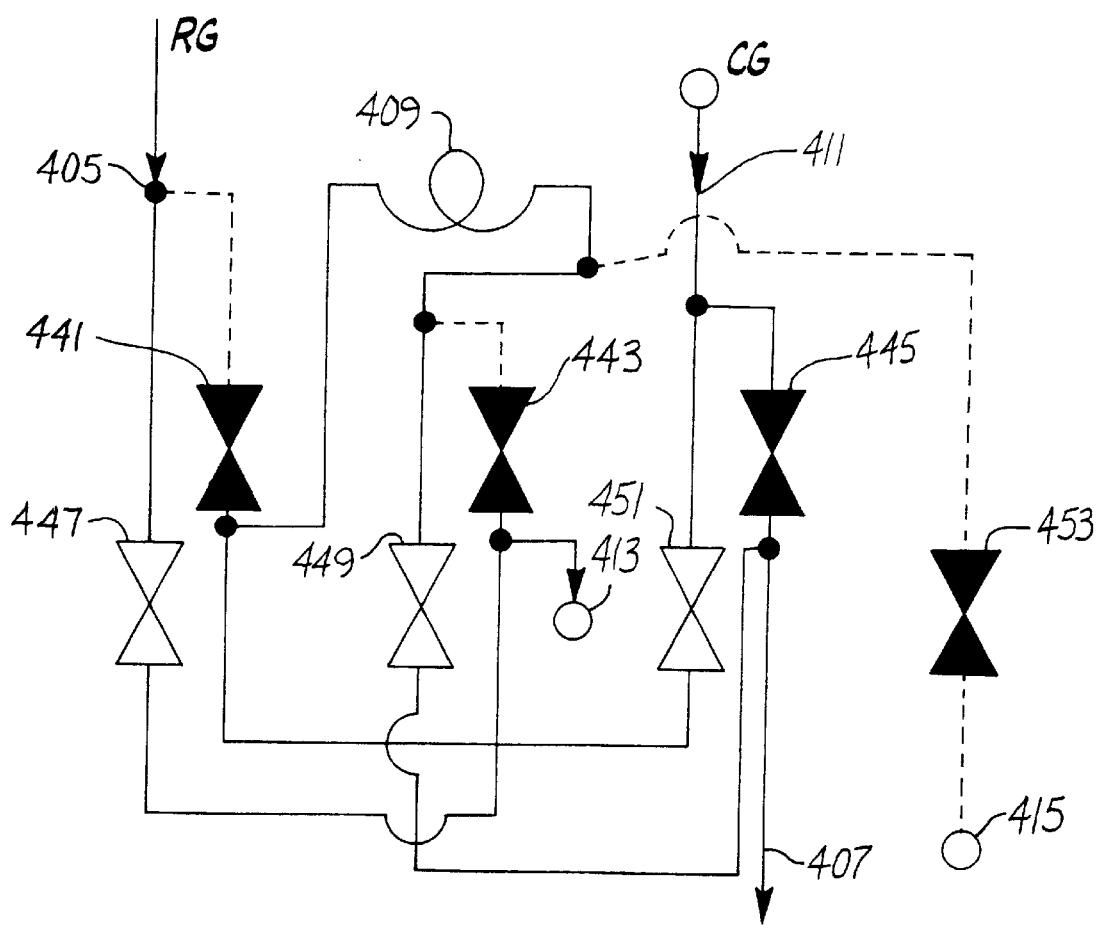
FIG. 7C is the diagrammatic representation of FIG. 7B but showing the flow circuit of the injection valve in a third actuation state.

Referring now to FIGS. 7A through 7C, a preferred operation of the valves will be described. In the preferred valving scheme of the present invention, microvalves 441 to 453 work in combination to provide the injection valve with three actuation states, for example, sample loading (FIG. 7A), sample depressurization (FIG. 7B) and sample injection (FIG. 7C). Referring to FIG. 7A, in the first actuation state of the injection valve, first microvalve 441, second microvalve 443 and third microvalve 445 are in a first, open position while fourth microvalve 447, fifth microvalve 449, sixth microvalve 451 and seventh microvalve 453 are in a second, closed position. Sample (or "reactant") gas entering the injection valve 401 at sample gas inlet passage 405 is directed to first microvalve 441 in the first, open position, wherein the sample gas enters gas sample loop 409. After passing through gas sample loop 409, the sample gas is directed to second microvalve 443 in a first, open position wherein the sample gas flows to waste outlet passage 413. Opening the loop 409 to the waste outlet passage 413 allows any old gas in the loop to be exhausted and allows the loop to be filled with the new sample gas. Simultaneously, carrier gas entering the injection valve at carrier gas inlet passage 411 is directed to third microvalve 445 in its first, open position, wherein the carrier gas flows to gas outlet passage 407 into a column of the gas chromatograph 121 (as shown in FIG. 1).

Referring now to FIG. 7B, in the second actuation state of the injection valve, the discrete charge of gas present in the gas sample loop 409 is captured and depressurized by switching first microvalve 441 and second microvalve 443 to the second, closed position while switching fourth microvalve 447 and seventh microvalve 453 to the first, open position. Thus, in the second actuation state of the injection valve, third microvalve 445, fourth microvalve 447 and seventh microvalve 453 are in a first, open position while first microvalve 441, second microvalve 443, fifth microvalve 449 and sixth microvalve 451 are in a second, closed position.

In the second actuation state, sample gas entering the injection valve at sample gas inlet passage 405 is directed to fourth microvalve 447 and flows to the waste outlet passage 413 instead of into the loop 409. Simultaneously, carrier gas CG entering the injection valve at carrier gas inlet passage 411 is directed to third microvalve 445 and flows to gas outlet passage 407, as in the first actuation state. Thus, it will be appreciated that the loop 409 is isolated from both incoming sample gas and incoming carrier gas in the second actuation state. By switching the seventh microvalve 453 to a first, open position, the discrete charge of gas present in the gas sample loop 409 is depressurized. Opening the seventh microvalve 453 allows vent passage 415 to be in fluid communication with the discrete gas sample charged to the gas sample loop 409, thus venting the gas sample loop to depressurize the sample collected in the loop.

Referring now to FIG. 7C, in the third actuation state of the injection valve, the discrete charge of gas captured in the sample loop is injected via the gas outlet passage 407 into the analysis apparatus 121 (FIG. 1) by switching fifth microvalve 449 and sixth microvalve 451 to a first, open position and switching third microvalve 445 and seventh microvalve 453 to a second, closed position. Thus, in the third actuation state, fourth microvalve 447, fifth microvalve 449 and sixth microvalve 451 are in a first, open position while first microvalve 441, second microvalve 443, third microvalve 445 and seventh microvalve 453 are in a second, closed position. In the third actuation state, sample gas entering the injection valve 401 at sample gas inlet passage 405 is still directed to fourth microvalve 447 and flows directly to waste outlet passage 413 as in the second actuation state described above. Thus, the loop 409 continues to be isolated from sample gas input at passage 407. Carrier gas entering the injection valve at carrier gas inlet passage 411 is directed to sixth microvalve 451 and flows to gas sample loop 409 to push the discrete charge of sample gas present in gas sample loop. Upon exiting gas sample loop 409, the sample gas and the carrier gas are directed to fifth microvalve 449 and flow to gas outlet passage 407 and into the analysis apparatus 121 where the sample gas is analyzed.

Each of the microvalves 441–453 described above may be independently actuated; however, in an even more preferred embodiment, first microvalve 441 and second microvalve 443 are conjointly actuated and fifth microvalve 449 and sixth microvalve 451 are conjointly actuated, as these pairs are always simultaneously in a first, open or second, closed position in the valving scheme described above. Thus, referring back to FIGS. 4 and 5, this valving scheme permits the seven microvalves 441–453 to be operated with only five actuation lines 432 connected to fifth plate 431.

In a fourth embodiment, the injection valves of the present invention are arranged in a parallel array of injection valves capable of controlling fluids from multiple sources substantially simultaneously. The parallel injection valve array may be built up from plural independent injection valve modules (e.g., as shown in FIG. 8A) or formed in a unitary body. For example, the parallel injection valve array may typically comprise a plurality of independent injection valve modules substantially similar to the injection valve 401 described above in relation to the third, preferred embodiment of the invention and illustrated in FIG. 4. Referring now to FIG. 8A, such a typical independent injection valve module generally comprises a valve body 503 including a sample gas inlet passage 505 adapted for connection to a line for receiving gas at different pressures, a gas outlet passage 507, and a gas sample loop 509.

Figure 8B:
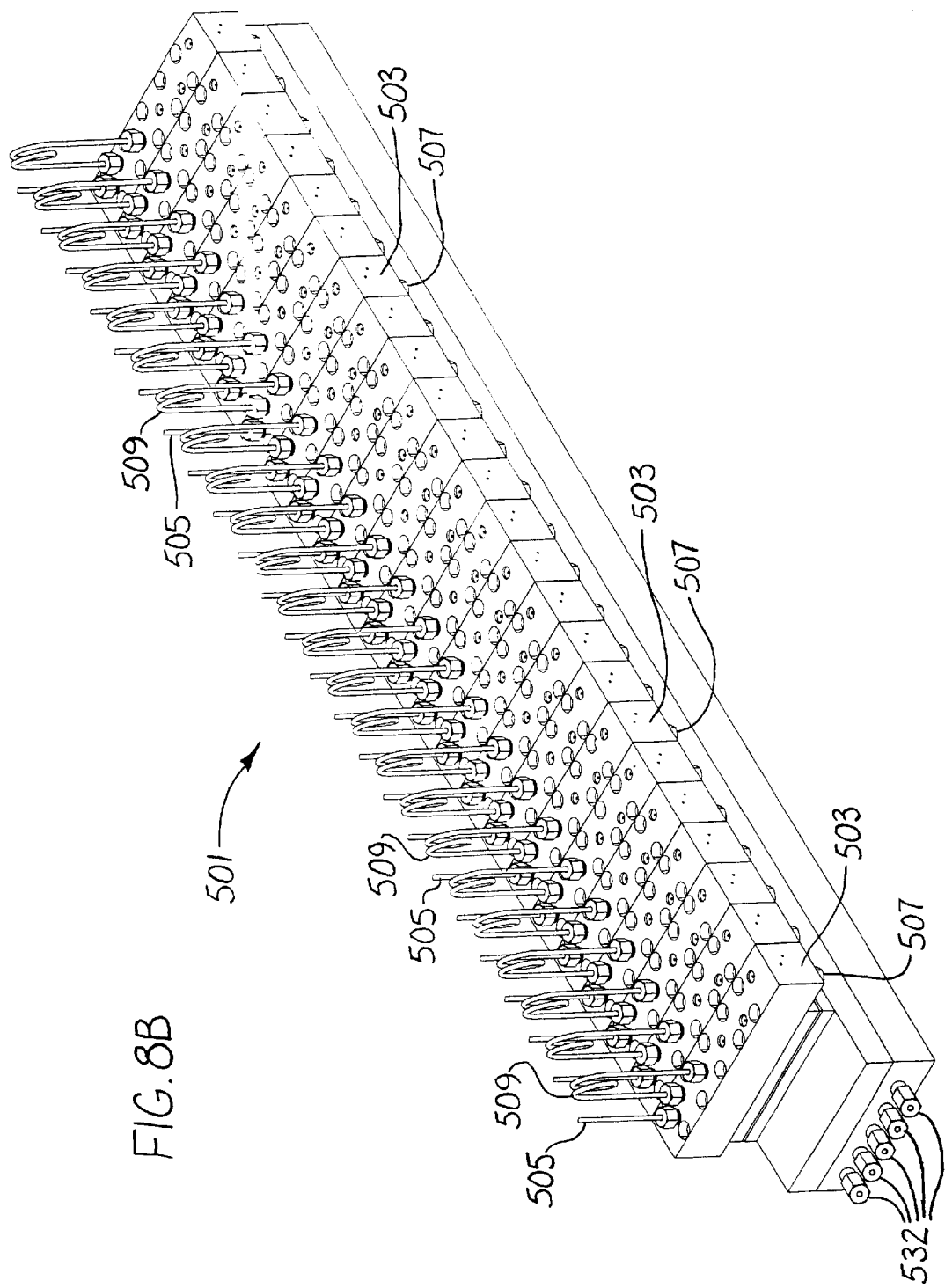
FIG. 8A is a perspective of a single, modular injection valve of the present invention; and, FIGS. 8B through 8D are perspective views of a fourth embodiment of the present invention comprising a parallel array of injection valves.

Referring now to FIGS. 8B through 8D, a parallel injection valve array is generally illustrated at 501. The injection valve array as illustrated comprises 24 independent injection valves, each of which are substantially similar to any of the injection valves described above. However, it is important to note that the injection valve arrays of the present invention may comprise any number of independent injection valve modules in combination for operation in parallel.

In a particularly preferred parallel array, the injection valves 501 are substantially similar to those described above in the third embodiment of the present invention. Thus, each injection valve of the parallel array is constructed and arranged for segregating fluid received into discrete samples, and to depressurize any sample having a pressure in excess of a predetermined maximum whereby samples leaving the injection valve array are of similar pressures. Further, each injection valve of the array comprises plural microvalves with at least some of the microvalves within each injection valve being independently operable from each other. Also, the injection valve array may be preferably configured with at least some of the injection valves interconnected for simultaneous actuation.

Referring now to FIG. 8B, a particularly preferred parallel array of the present invention generally comprises a plurality of individual injection valve bodies 503, each of which include a sample gas inlet passage 505 adapted for connection to a line for receiving gas at different pressures, a gas outlet passage 507, and a gas sample loop 509. Preferably, each of the individual valve bodies are substantially similar to the valves of the third embodiment of the invention as described above, each having a valving scheme to be operated by five actuation lines 532.

Referring now to FIG. 8C, the parallel array of the present invention may further be adapted to engage a heater block 550 for heating the gas in the injection valves 501. Heater block 550, while not necessary or critical to the instant invention, may be used in particular applications of the invention in which it is desired to heat the gases while in the injection valve (e.g., to avoid condensation of the sample gas). Likewise, any of the embodiments described above may include a heater block within the scope of the present invention.

The individual injection valves in the parallel array are connected to a carrier gas manifold 560 which supplies carrier gas to each injection valve. The manifold 560 also contains portions of the gas outlet passages, waste outlet passages and vent passages. Tubes 561 extending from the manifold carry depressurized samples in parallel to the gas chromatograph 121 (as shown in FIG. 1).

The injection valves of the array may be of any geometrical arrangement as described above with the array comprising a linear or curvilinear arrangement of side-byside injection valves. However, it is preferred that the injection valves be linear to achieve a high spatial density within the array. Thus, parallel injection valve arrays may be advantageously constructed having an injection valve density of at least one injection valve every 10 cm of linear or curvilinear length of the array, for example, one injection valve every 6 cm, 4 cm, 3 cm, 2 cm, 1 cm, 0.5 cm, 1 mm or less.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than those listed.

As various changes could be made in the above constructions without departing from the scope of the invention, it is intended that all matter contained in the above description or shown in the accompanying drawings shall be interpreted as illustrative and not in a limiting sense. In view of the above, it will be seen that the several objects of the invention are achieved and other advantageous results attained.

What is claimed is:

1. A microvalve assembly for use in receiving gas at different pressures and emitting discrete charges of gas at approximately the same pressure, the microvalve assembly comprising:

a valve body having a gas inlet passage adapted for connection to a line for receiving gas at different pressures, a gas outlet passage, a gas charge loop and a pressure control port;

a first microvalve associated with the valve body adapted to admit gas passing into the gas inlet passage into the gas charge loop in a first position of the valve and to block entry of gas from the gas inlet passage into the gas charge loop in a second position;

a second microvalve associated with the valve body adapted to open the gas charge loop to the pressure control port for reducing the pressure of gas in the gas charge loop in a first position and to block the gas charge loop from the pressure control port in a second position;

a third microvalve associated with the valve body adapted to open the gas charge loop to the gas outlet passage for emitting the discrete charge of gas from the gas loop from the valve body in a first position and to block the gas charge loop from the gas outlet passage in a second position.

2. A microvalve assembly as set forth in claim 1 wherein the valve body further comprises a carrier gas inlet passage for receiving a carrier gas into the valve body, the microvalve assembly further comprising a fourth microvalve adapted to admit carrier gas into the gas charge loop in a first position when the third microvalve is in said first position for pushing the gas in the gas charge loop out of the gas outlet passage and to block flow of carrier gas into the gas charge loop in a second position.

3. A microvalve assembly as set forth in claim 2 further comprising a fifth microvalve adapted to permit flow of carrier gas from the carrier gas inlet passage to the gas outlet passage in a first position and to block carrier gas from the gas outlet passage in a second position.

4. A microvalve assembly as set forth in claim 3 wherein the valve body further comprises a waste outlet passage, the microvalve assembly further comprising a sixth microvalve adapted to permit passage of gas in the gas charge loop into the waste outlet passage in a first position when the first valve is in the first position and to block flow of gas from the gas charge loop to the waste outlet passage in a second position, and a seventh microvalve adapted to permit passage of gas in the gas inlet passage into the waste outlet passage in a first position when the first microvalve is in the second position and to block flow of gas from gas inlet passage to the waste outlet passage in a second position.

* * * * *